United States Patent
Helf et al.

(10) Patent No.: US 6,293,474 B1
(45) Date of Patent: Sep. 25, 2001

(54) DELIVERY SYSTEM FOR DISPENSING VOLATILES

(75) Inventors: Thomas A. Helf, Waukesha; Edward J. Martens, III; David A. Tomkins, both of Racine, all of WI (US)

(73) Assignee: S. C. Johnson & Son, Inc., Racine, WI (US)

(*) Notice: Subject to any disclaimer, the term of this patent is extended or adjusted under 35 U.S.C. 154(b) by 0 days.

(21) Appl. No.: 09/498,859

(22) Filed: Feb. 7, 2000

Related U.S. Application Data

(60) Provisional application No. 60/123,206, filed on Mar. 8, 1999.

(51) Int. Cl.[7] .................. B05B 1/08; B05B 3/04
(52) U.S. Cl. ................... 239/102.2; 239/102.1
(58) Field of Search ............... 239/102.1, 102.2, 239/4; 346/140.1, 141; 347/6, 9, 20, 47, 68, 70

(56) References Cited

U.S. PATENT DOCUMENTS

| | | | |
|---|---|---|---|
| 3,572,590 | * 3/1971 | Malone | 239/327 |
| 3,738,574 | 6/1973 | Guntersdorfer et al. | 239/102 |
| 3,790,079 | 2/1974 | Berlung et al. | 239/3 |
| 3,799,731 | 3/1974 | Novak | 431/313 |
| 4,113,809 | 9/1978 | Abair et al. | 261/81 |
| 4,294,407 | 10/1981 | Reichl et al. | 239/102 |
| 4,384,589 | * 5/1983 | Morris | 132/88.5 |
| 4,454,877 | 6/1984 | Miller et al. | 128/200.21 |
| 4,739,928 | 4/1988 | O'Neil | 239/45 |
| 4,793,339 | 12/1988 | Matsumoto et al. | 128/200.16 |
| 4,877,989 | 10/1989 | Drews et al. | 310/323 |
| 5,312,281 | 5/1994 | Takahashi et al. | 446/25 |
| 5,382,410 | 1/1995 | Peltier . | |
| 5,518,179 | 5/1996 | Hjumberstone et al. | 239/102.2 |
| 5,529,055 | 6/1996 | Gueret | 128/200.16 |
| 5,716,002 | * 2/1998 | Haack et al. | 239/102.2 |
| 5,803,362 | 9/1998 | Fraccaroll | 239/102.2 |
| 5,823,434 | * 10/1998 | Cooper | 239/102.2 |
| 5,848,751 | * 12/1998 | Wang et al. | 239/102.1 |
| 5,916,493 | 6/1999 | Miller | 261/154 |
| 5,921,232 | 7/1999 | Yokoi et al. | 128/200.14 |
| 5,938,117 | 8/1999 | Ivri | 239/4 |
| 5,996,903 | * 12/1999 | Asai et al. | 239/102.1 |
| 6,010,333 | 1/2000 | Tendick | 431/324 |

\* cited by examiner

*Primary Examiner*—David A. Scherbel
*Assistant Examiner*—Davis Hwu

(57) ABSTRACT

Disclosed herein is a piezoelectric liquid delivery system or atomizer for production of droplets of liquid or liquid suspensions by means of a battery operated continuous action dispenser utilizing an orifice plate in communication with a piezoelectric element. By use of a wick having specified properties and high compliance, superior results are achieved.

20 Claims, 4 Drawing Sheets

DELIVERY SYSTEM FOR DISPENSING VOLATILES

PRIORITY

Figure 1:
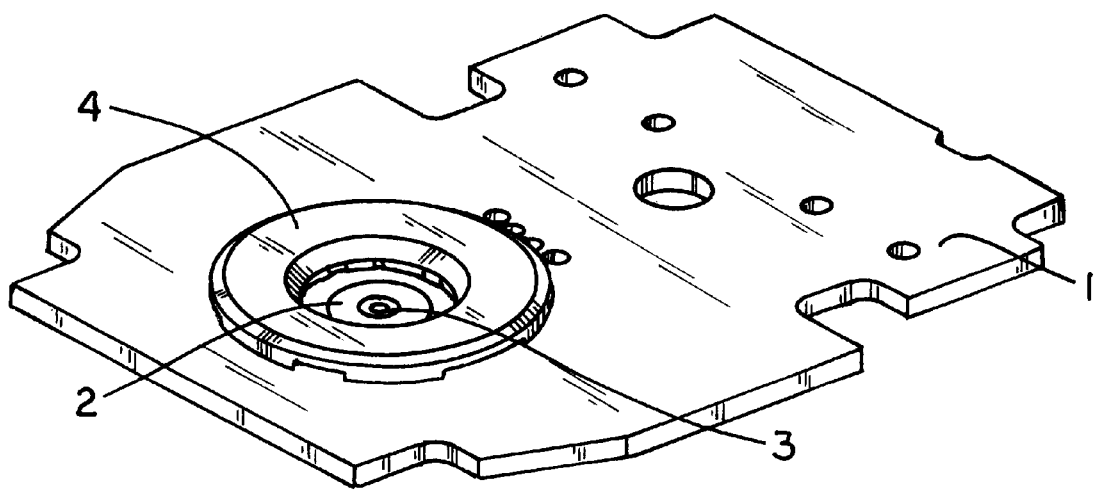

This application claims the benefit of U.S. Provisional Application No. 60/123,206, filed Mar. 8, 1999.

TECHNICAL FIELD

The present invention relates to means for the distribution of a liquid active material, such as a perfume, air freshener, insecticide formulation, or other material, in the form of fine particles or droplets, as in a fine spray, by means of a piezoelectric device. In particular, the invention is directed to a piezoelectric liquid delivery system for the production of droplets of liquid, or liquid suspension, by means of an electomechanical or electroacoustical actuator. More specifically, the present invention relates to a battery operated dispenser utilizing an orifice plate in communication with a piezoelectric element. By proper selection of the means for transfer of the liquid from its container to the orifice plate, an improved method for dispensing such liquids is achieved.

BACKGROUND ART

The distribution of liquids by formation of a fine spray, or atomization, is well known. One method for such distribution is to atomize a liquid by means of the acoustic vibration generated by an ultrasonic piezoelectric vibrator. An example of such a method is shown in Carter, U.S. Pat. No. 4,702,418, which discloses an aerosol dispenser including a nozzle chamber for holding fluid to be dispensed, and a diaphragm forming at least a portion of the chamber. An aerosol dispensing nozzle is disposed therein, with a restrictive passage for introducing liquid from the reservoir to the nozzle. A pulse generator in combination with a low voltage power source is used to drive a piezoelectric bender, which drives fluid from the reservoir through the nozzle to create an aerosol spray.

Another atomizer spraying device is shown by Humberstone et al, in U.S. Pat. No. 5,518,179, which teaches a liquid droplet production apparatus comprising a membrane which is vibrated by an actuator which has a composite thin-walled structure, and is arranged to operate in a bending mode. Liquid is supplied directly to a surface of the membrane and sprayed therefrom in fine droplets upon vibration of the membrane.

U.S. Pat. Nos. 5,297,734 and 5,657,926, of Toda, teach ultrasonic atomizing devices comprising piezoelectric vibrators with a vibrating plate connected thereto. In U.S. Pat. No. 5,297,734, the vibrating plate is described as having a large number of minute holes therein for passage of the liquid, and as being in physical contact with a liquid keeper such as a sponge.

In U.S. Pat. No. 4,301,093, Eck teaches the use of a wick of elastically resilient material which presses against the vibrating atomizer element, and covibrates with a more or less damped vibration amplitude. A wick tube surrounds the wick almost to the point of contact with the vibrating element.

Ivri et al, in U.S. Pat. No. 5,586,550, teach apparatus for the delivery of therapeutic liquids, including a vibratable non-planar member having tapered apertures, to which liquid is delivered by squeezing a liquid reservoir to deposit it directly on the surface, such that all of the liquid adheres to the vibratable member by surface tension. A piezoelectric element is bonded to a vibratory cantilever beam to provide oscillation to the carrier plate in contact with the non-planar member so as to nebulize the liquid in contact therewith.

Japanese Patent Publication 06320083A discloses an ultrasonic atomizer wherein a strong liquid storing material (e.g. a sponge) delivers liquid to a perforated diaphragm which is oscillated in response to piezoelectric vibration. The contact pressure of the liquid storing material against the diaphragm is kept constant by a spring tensioning device.

While a number of additional patents disclose means for the dispersion of liquids by ultrasonic atomization, or for timed intervals of dispersion, they have achieved only moderate success. See, for example, U.S. Pat. Nos. 3,543,122, 3,615,041, 4,479,609, 4,533,082, and 4,790,479. The disclosures of these patents, and of all other publications referred to herein, are incorporated by reference as if fully set forth herein.

However, such atomizers and/or dispensers fail to provide a system by which liquid to be dispersed is supplied to the vibratory mechanism/surface without resulting in damping of the piezoelectric vibrational frequency. Moreover, the prior art has failed to provide an easily portable, battery operated, continuous-action dispenser employing an orifice plate in mechanical connection with a piezoelectric element, capable of long periods of use with little or no variation in the delivery rate. Thus, a need exists for improved atomizers or dispensers for use in distribution of active fluids such as fragrances and insecticides, having improved means for supply of the fluid to be dispensed to the vibrating orifice surface.

DISCLOSURE OF INVENTION

It is an object of the present invention to provide a highly efficient, consistent, and reliable dispenser for liquid active materials, employing an orifice plate in mechanical connection with a piezoelectric element. By liquid active materials, it is meant to include such liquids as perfumes, air fresheners, household cleaning materials, disinfectants, repellants, insecticides, aroma therapy formulations, medicinals, therapeutic liquids, or other liquids or liquid suspensions which benefit from atomization for use. These compositions may be aqueous, or comprise various solvents. In a preferred embodiment of the invention, the piezoelectric liquid delivery system is easily portable, battery operated, and conveniently refillable with the same, or a different, liquid active.

It is a further object to provide a piezoelectric pump capable of operating efficiently for months, on low voltage batteries, while maintaining consistency of delivery throughout the period. Included in such object is to provide a piezoelectric atomizer capable for use with such electrical sources as 9 volt batteries, conventional dry cells such as “A”, “AA”, “AAA”, “C”, and “D” cells, button cells, watch batteries, and solar cells or solar power. The preferred energy sources for utilization in combination with the present invention are “AA” and “AAA” cells.

In still another object, it is desired to provide a liquid delivery system capable of atomizing fragrance oil or insecticide formulation linearly over time, while maintaining the same character/composition on the last day as was delivered on the first, i.e. with no component change or separation with time, and with no variation in volume of liquid dispersed per activation of the system. The electronics of such a unit are preferably programmable, and may be used to set a precise delivery rate (e.g., in milligrams per hour, or mg/hr.), or may allow the consumer to adjust intensity or effectiveness to a desired level for personal preference, efficacy, or for room size.

Another object of this invention is to provide small droplets of pure fragrance or insecticide formulation which are propelled intermittently from the unit to form a small "cloud" or "puff," which droplets quickly diffuse and move throughout a large area on air currents present in said area. It is found that the small size of such particles, and the correspondingly large ratio of surface area to mass, result in these droplets evaporating quickly and uniformly. In preferred embodiments, the delivery system operates with a linear delivery rate for several months on a single 1.5 volt "AA" size battery, delivering uniform volumes of essentially equally sized droplets of the liquid for the entire period.

These and other objects of this invention are achieved by an atomizer for fragrances, insecticide formulations, and other liquids such as set forth previously, wherein the atomization system includes a chamber for the liquid to be dispensed, means to supply the liquid from said chamber to an orifice plate for dispersal of the liquid, a piezoelectric element, an energy source, and circuitry to drive and control the piezoelectric element. The fragrance or insecticide formulation is supplied to the back side of the orifice plate through a capillary feed system that delivers the liquid to the orifice plate, but does not exert sufficient pressure against the orifice plate to damp the vibrational frequency to which the plate is subjected by the piezoelectric element. The piezoelectric element may be driven by circuitry powered by a small battery, capable of exciting the element and causing it to force liquid through the orifice plate, which has a multitude of small tapered or conical holes therein, perpendicular to the surfaces thereof, the exit of said holes being on the order of from about 1 to about 25 microns, preferably from about 4 to about 10 microns, and most preferably from about 5 to about 7 microns in diameter. Timing circuitry is used to provide an intermittent excitation to the piezoelectric element so as to dispense small droplets of said liquid in a time dependent fashion. We have learned that the use of a highly compliant wick material, having the ability to remain in contact with the orifice plate without damping the vibration thereof, will provide superior transfer of the liquid to the orifice plate, resulting in superior operation.

These and still other objects and advantages of the present invention will be apparent from the description which follows. However, the claims should be looked to in order to understand the full scope of the invention.

BRIEF DESCRIPTION OF DRAWINGS

FIG. 1 is a partial isometric view of a circuit board suitable for use in a piezoelectric atomizer in accordance with a preferred embodiment of the present invention.

FIG. 2 is an isometric view of a liquid container and liquid transport means suitable to bring the liquid to the surface of the orifice plate.

FIG. 3 is a cross sectional view showing the relationship of the liquid container, the feed means, and the piezoelectric element.

FIG. 4 is a magnified detail of the area of FIG. 3 enclosed within the circle.

FIG. 5 is a top view of the piezoelectric element and the printed circuit board mounted on the chassis of a preferred embodiment FIG. 6 illustrates a much simplified cross-sectional diagram of a piezoelectric pump assembly suitable for use with a preferred embodiment of the present invention.

MODES FOR CARRYING OUT THE INVENTION

It is to be understood that the Figures, and the discussion below, are directed to preferred embodiments of the invention, but that the invention itself is broader than the illustrations given. Specifically, the invention is equally applicable to other forms of piezoelectric atomization, such as the use of cantilever beams and/or amplifying plates, as well as atomizers driven by conventional electric power, i.e. wall plug, rather than battery powered.

FIG. 1 illustrates the general relationship between the printed circuit board, 1, in which the piezoelectric element 2 is located. The circuit board, 1, is illustrated without the electronic circuitry and battery associated therewith for clarity and ease of understanding of the present invention. It is also to be understood that the circuit board may, in use, be attached to the chassis of a dispenser, which chassis is in turn placed in a decorative shell-like housing or receptacle (not shown) for use. The chassis board 11 is shown in top view in FIG. 5, while the housing is not illustrated. The decorative receptacle or housing may be of any form or shape suitable for the purpose of retaining and protecting the elements of the dispenser while providing a pleasing appearance to the consumer, and permitting passage of the liquid, in spray form, from the dispenser to the atmosphere. As such, the dispenser housing may be advantageously produced by high speed molding of any material suitable for use with, and contact with, the liquid to be dispensed.

Piezoelectric element 2 may be mounted as illustrated in the circuit board 1, held in place by grommet 4, or by any similar suitable means which does not inhibit vibration of the element. The piezoelectric element 2, in the form of a ring, is positioned in a concentric relationship to the orifice plate 3, and is attached to the orifice plate flange so as to be in vibratory communication therewith. The piezoelectric element generally comprises a piezoelectric ceramic material, such as a lead zirconate titanate (PZT) or lead metaniobate (PN), but may be any material exhibiting piezoelectric properties.

The orifice plate comprises any conventional material suitable for the purpose, but is preferably comprised of an electroplated nickel cobalt composition formed upon a photoresist substrate which is subsequently removed in conventional manner to leave a uniform porous structure of nickel cobalt having a thickness of from about 10 to about 100 microns, preferably from about 20 to about 80 microns, and most preferably about 50 microns. Other suitable materials for the orifice plate may be utilized, such as nickel, magnesium-zirconium alloy, various other metals, metal alloys, composites, or plastics, as well as combinations thereof. Other suitable materials may be used, having the appropriate grain size and wetting properties. By forming the nickel cobalt layer through electroplating, a porous structure having the contour of the photoresist substrate may be produced, in which permeability is achieved by formation of conical holes having a diameter of about 6 microns on the exit side, and a larger diameter on the entrance side. The orifice plate may be planar, but is preferably dome shaped, i.e. somewhat elevated at the center, but may vary from flat to parabolic, arc shaped, or hemispherical in shape, or any other suitable shape which enhances performance. The plate should have a relatively high bending stiffness, to assure that the apertures therein shall be subject to essentially the same amplitude of vibration, so as to simultaneously eject droplets of liquid which are uniform in diameter.

While shown in the form of a concentric ceramic piezoelectric element surrounding an orifice plate or aperture, it is also conceived that the present invention is also suitable for use with a conventional piezoelectric element comprising an oscillator and a cantilever beam in contact with a diaphragm, nozzle, or orifice plate suitable for dispersion of liquid droplets or fog.

Figure 2:
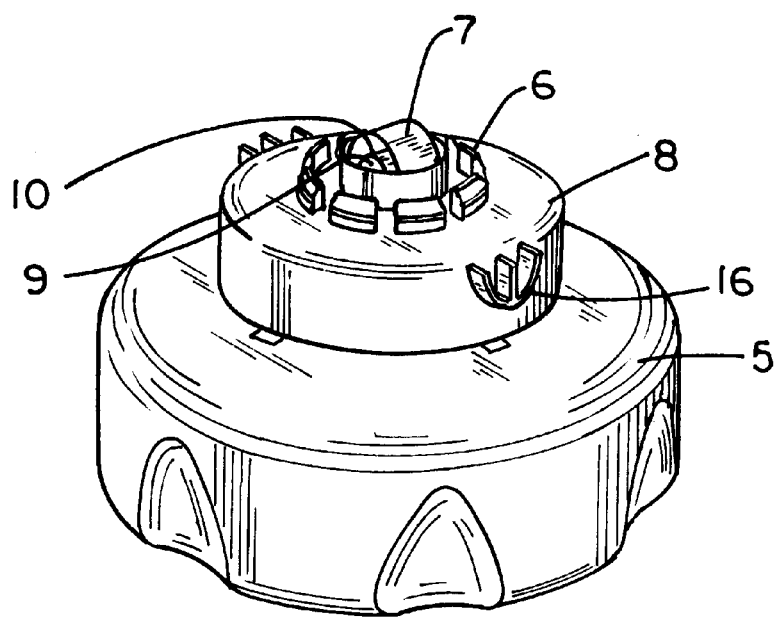

Shown in FIG. 2 is the liquid container 5 for storage and provision of the fragrance, air freshener, insect control liquid, or other material to be dispensed. As illustrated, the container is closed by a closure 8. Also shown are bayonet clips 6, which are present to hold a removable top closure, or cap, not shown, which is used in transport and storage of the container, and may be removed easily when it is desired to put the container into the dispenser and permit use of the contents thereof. From bottle opening 9, exiting through the closure 8, projects the liquid supply means 7, a loop shaped wick or dome shaped liquid feed medium. For convenience, we shall refer to the liquid supply means as a wick, although it may comprise a number of varying shapes and materials, from hard capillary systems to soft porous wicks, or strips of cloth. The function of the wick is to transport liquid from container 5 to a position in contact with the orifice plate. Accordingly, the wick should be unaffected by the liquid being transported, porous, and permit compliance with the orifice plate. The porosity of the wick should be sufficient to provide a uniform flow of liquid throughout the range of flexibility of the wick, and in any configuration thereof. To best transport the liquid to the surface of the orifice plate, it has been found necessary that the wick itself physically contact the plate to transfer the liquid to the orifice plate. Liquid is preferably delivered to the orifice plate in such a manner that essentially all delivered liquid will adhere to and transfer to the plate surface by surface tension. Among suitable wick materials, we have found it preferable to utilize such materials as paper, or fabrics of cotton, nylon, polypropylene, fiber glass, etc. It is preferred that the wick comprise a highly porous material, having porosity and softness similar to a filter paper or tissue. We have found that a preferred wick material comprises a 100 percent cotton fiber cloth wick provided by Spring Industries, having a thread count of 68×68, in a broadcloth weave, with a density of about 7.2 grams per 100 square inches (about 93.2 grams or 3.3 ounces per square yard). A loop of this cloth is utilized as the wick, in a shape of a strip about 0.1255 inches wide, 2.75 inches long, and 0.01 inches thick. The preferred height of the loop, above the wick holder, is preferably from about 0.05 to about 0.15 inches, more preferably from about 0.07 to about 0.10 inches, and most preferably from about 0.08 to about 0.09 inches. The height of the loop, however, is dependent upon design of the refill container and the atomizer, and the joined configuration thereof. The wick may preferably be shaped to conform to the surface of the orifice plate to which it is juxtaposed, and held in the correct position by the wick holder or positioner, 10, located in the bottle opening 9, of the closure 8 of liquid container 5. Liquid will flow readily from the wick to the plate as a result of the viscosity and surface tension of the liquid. It is to be noted that the wick is intended to be included as an integral part of a liquid resupply unit, which will comprise the container, the liquid, the bottle closure, the wick, and the wick holder or positioner, as well as a top closure to seal the unit for storage and shipment. Such a unit may thus comprise a refill bottle for the dispenser, suitable to be placed in the dispenser at the consumers convenience. To this end, the liquid container 5 may have attachment means 16 on the bottle closure 8, for insertion into a suitable receiving means in the chassis 11 to lock it in operative position, after removal of the top closure or cap. The wick may also be provided as an integral part of the orifice plate, chassis, or another part of the atomizer assembly, with means provided, such as wick tails, to transfer the liquid to the wick from the liquid reservoir.

Figure 3:
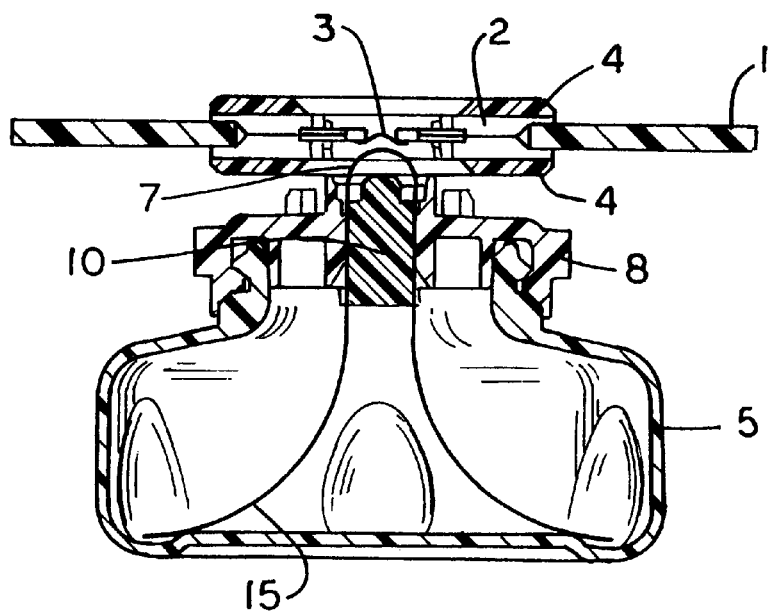
Figure 4:
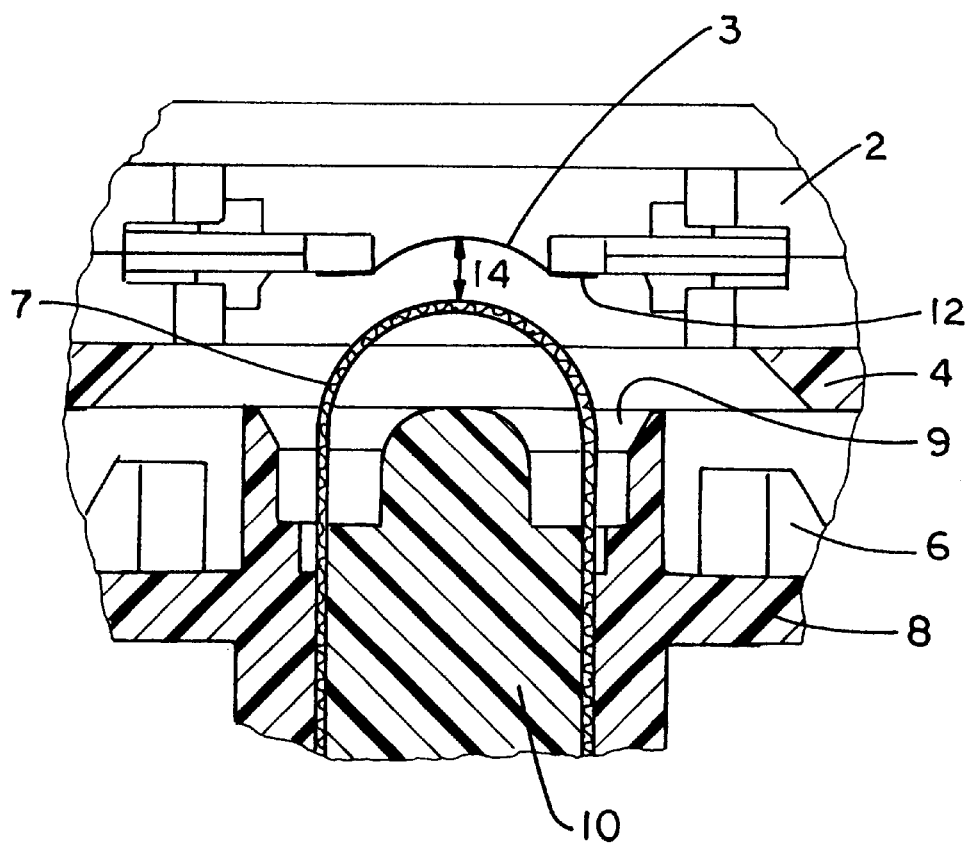
Figure 6:
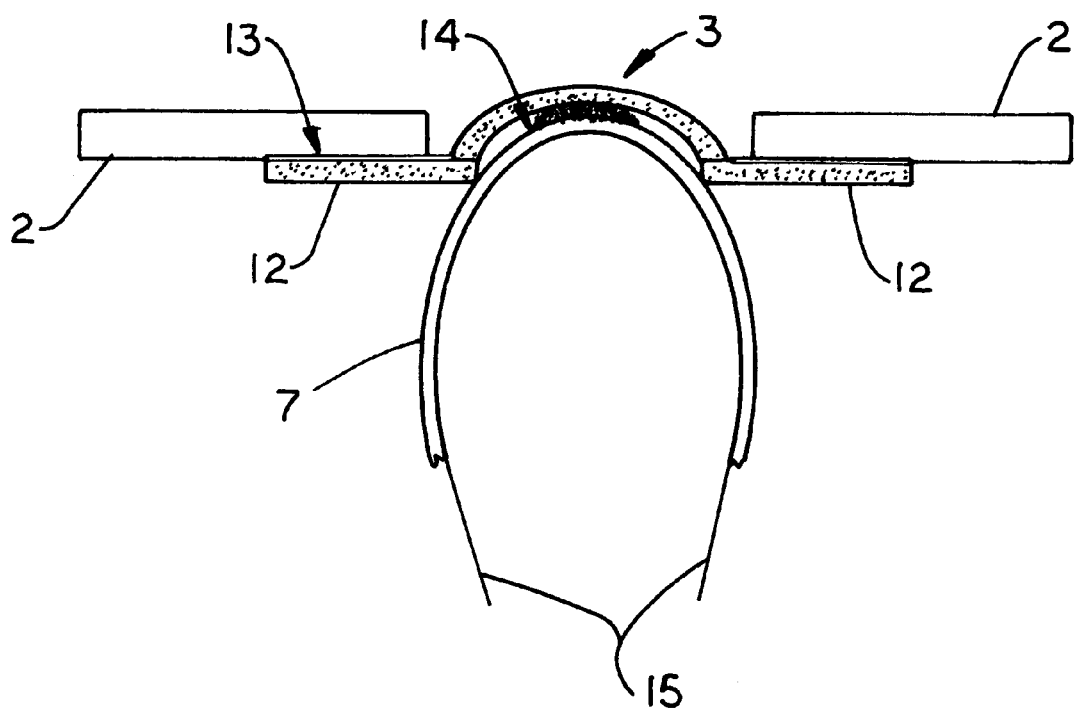

FIG. 3 illustrates, in cross sectional view, the relationship between the liquid container 5, the wick 7, the piezoelectric element 2, and the orifice plate 3 of a specific preferred embodiment of the invention. The piezoelectric element 2 is positioned, for example, in printed circuit board 1, by grommets 4, or by any suitable means which does not restrict vibration of the piezoelectric element. In a preferred embodiment of the invention, the concentric piezoelectric element surrounds the orifice plate 3, in mechanical connection therewith. The orifice plate is, in turn, in contact with the wick 7, permitting the liquid to be dispensed from the container 5 to the orifice plate, where transfer occurs through surface tension contact. Not shown is the chassis board 11 of the dispenser, which holds the circuit board 1 and the liquid container in the appropriate position to bring wick 7 into juxtaposition with the orifice plate 3. Wick 7 is held in the opening of closure 8 by the wick holder 10, which permits a degree of freedom to the flexible wick 7, so as to allow a range of adjustment thereof, while wick tail 15 assures complete utilization of all the liquid in the container 5. This degree of freedom permits self-adjustment of the wick relative to the surface of the orifice plate, to compensate for variations in position resulting from the vagaries of manufacture and shipment, and provides for a compliant feed means for transfer of the liquid from the container to the face of the orifice plate. As will be apparent to one skilled in the art, the height of the wick, as shown in FIGS. 3 and 4, may be adjusted to vary the liquid gap 14, as shown in FIGS. 4 and 6, and to assure an appropriate degree of contact between the wick and the plate. For a more detailed view of the relationship between the wick and the orifice plate, attention is directed to FIG. 4, a magnified detail of a section of FIG. 3, wherein is shown the looped wick 7, in juxtapostion with domed orifice plate 3, in which the liquid to be transferred is in surface tension contact with the orifice plate. While FIG. 4 shows the wick and the plate as in contact throughout the full arc of the dome of the orifice plate, it is to be understood that this is for illustration only, and that plate 3 may in fact contact wick 7 for only a limited arc (as shown in FIG. 6) to achieve transfer of the liquid, dependent upon viscosity, surface tension, and temperature of the liquid, as well as the specific porosity and flexibility of the wick., and the extent of the liquid gap 14. As shown, the passage of the wick 7 through the opening 9 in the closure element 8 is controlled by the wick holder/positioner 10. FIG. 4 also shows the mounting grommet 4 for the piezoelectric element 2, orifice plate 3, and the orifice plate flange 12, as well as the clips 6 which hold the removable cap (not shown) to the bottle closure 8.

Figure 5:
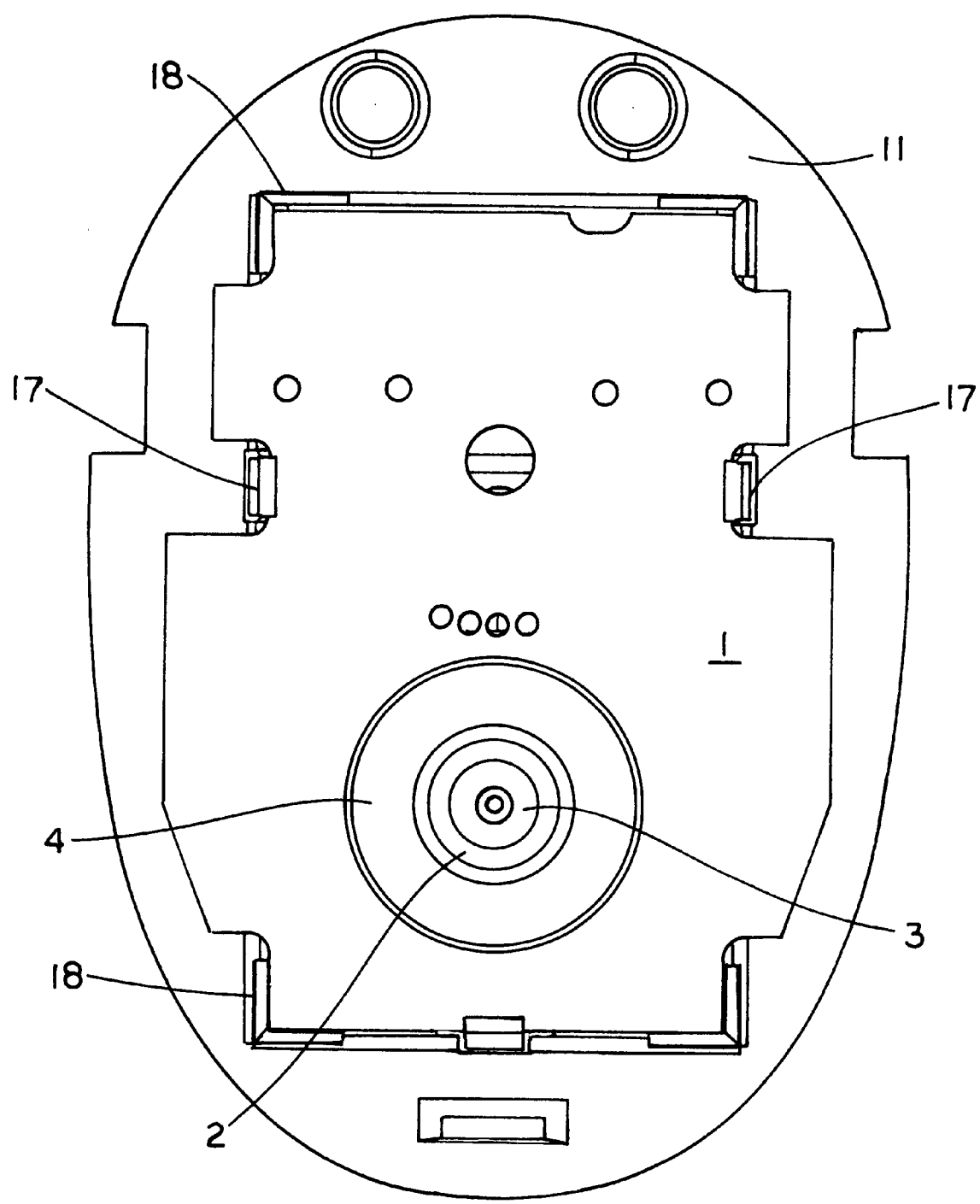

FIG. 5 is a top view, showing the relationship of circuit board 1, piezoelectric element 2, orifice plate 3, mounting grommet 4, and the chassis board 11. As previously indicated, the piezoelectric element 2, in concentric relationship to the orifice plate 3, is held in place in the circuit board 1 by the grommet 4. The circuit board is mounted on chassis board 11 in conventional manner, such as with clips 17 and positioning brackets 18.

In FIG. 6, a simplified cross sectional diagram of the invention illustrates the overall relationship of various elements. The orifice plate 3 is shown as including orifice plate flanges 12, which are in turn attached to the piezoelectric element 2 by suitable attachment means 13, such as epoxy adhesive. The wick 7 is illustrated in partial contact with the orifice plate 3, creating liquid gap 14, in which the liquid to be dispensed is transferred to the orifice plate. The wick is shown as also comprising fabric tails 15, which extend into the liquid container 5, not shown.

As indicated above, it has been learned that specific combinations of improvements in the elements and methods of use of the dispenser described result in surprisingly superior results. In particular, it has been found that the use of a highly compliant and flexible wicking material will assure a better transfer of liquid from the liquid container to the orifice plate surface. While such control is most beneficial in the preferred embodiment of the dispenser apparatus as described, it has been found to be of benefit in dispensers of varying configuration and elements.

The wick, 7, has been found to be a critical element of an improved atomizer for liquids such as perfumes, air fresheners, insecticide formulations., and other liquid actives as previously described. In the past, substantial contact of the wick with the orifice plate has been acknowledged as necessary to provide sufficient liquid transfer, but having a negative, damping effect thereupon. That is, physical contact between commonly used wick materials and the orifice plate has resulted in poor performance of the dispenser due to damping of the vibrations of the piezoelectric element. Conversely, poor contact between the wick and the plate has resulted in insufficient liquid delivery, and sporadic operation. We have now discovered that the compliance of the wick is critical to performance of the atomizer. Stiffer, i.e. less compliant, loops, such as nylon or polypropylene woven cloth of weights similar to the preferred cotton cloth wick described previously, gave unsatisfactory results. While the nylon and polypropylene cloths tested were found to be unsatisfactory, it is recognized that other forms or weights of such materials may perform satisfactorily. The key element to satisfactory operation and liquid feed to the vibrating orifice plate has been found to be the compliance of the wicking material. When the compliance of the wick is appropriate, damping of the vibrating orifice plate is negligible.

INDUSTRIAL APPLICABILITY

The atomization systems of the present invention can be used to automatically dispense such liquids as air fresheners, perfumes, or insecticides, to any given environment, over an extended period of time, with the advantage of uniformly dispensing equal amounts of liquid to the atmosphere over the life span of the battery which drives the dispenser. Further, the dispenser may be reused at will by means of refills and replacement batteries, so that the consumer may change the liquid being dispersed to the atmosphere as desired, with the added advantage that the amount of liquid being dispersed may be varied to adjust intensity or effectiveness to a desired level for personal preference, efficacy, or for room size.

While the present invention has been described with respect to what are at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

What is claimed is:

1. In an atomizer for dispensing a liquid active material, the combination of, a container for said liquid, an orifice plate having apertures therein, said plate being vibrated by a piezoelectric element, a capillary feed mechanism positioned to supply said liquid from said container to said orifice plate, said capillary feed mechanism comprising a highly porous and compliant wick and a wick holder arranged to hold said wick in a position such that it contacts the orifice plate to provide liquid to said orifice plate, the compliance of said wick being appropriate to cause negligible damping of said orifice plate.

2. A vibrator atomizer comprising:

an orifice plate having a plurality of fine orifices extending therethrough;

an actuator connected to vibrate said plate; and a wick element extending from within said reservoir to and contacting said plate in a manner which does not interfere with its vibration, said wick element comprising a cotton fiber cloth, said wick element being formed as a broadcloth weave.

3. A vibratory atomizer according to claim 2, wherein said wick element has a thread count of about 68×68 and a density of about 7.2 grams per 100 square inches.

4. A vibrator atomizer according to claim 2, wherein said wick element is shaped to conform to the surface of said orifice plate.

5. A vibrator atomizer according to one of claims 2–4, wherein said wick is looped where it touches said orifice plate.

6. A vibratory atomizer according to one of claims 2—4, wherein said actuator comprises a piezoelectric element.

7. A vibratory atomizer according to claim 5, wherein said actuator comprises a piezoelectric element.

8. A vibrator atomizer according to claim 3, wherein said wick element is shaped to conform to the surface of said orifice plate.

9. A vibratory atomizer comprising:

a liquid reservoir;

an orifice plate having a plurality of fine orifices extending therethrough;

an actuator connected to vibrate said plate; and a wick element extending from within said reservoir to and contacting said plate in a manner which does not interfere with its vibration, said wick element comprising a fiber cloth and being looped at the region thereof which contacts said orifice plate.

10. A vibratory atomizer according to claim 9, wherein said wick element is formed of cotton.

11. A vibratory atomizer according to claim 10, wherein said wick element is formed as a broadcloth weave.

12. A vibratory atomizer according to claim 11, wherein said wick element has a thread count of about 68×68 and a density of about 7.2 grams per 100 square inches.

13. A vibratory atomizer according to one of claims 9–12, wherein said wick element is shaped, where it is looped, to conform to the surface of said orifice plate.

14. A vibratory atomizer according to one of claims 9–12, wherein said actuator comprises a piezoelectric element.

15. A vibratory atomizer according to claim 13, wherein said actuator comprises a piezoelectric element.

16. A refill container for a vibratory type atomizer having an orifice plate which vibrates to atomize a liquid into the atmosphere in the form of very small droplets, said refill container comprising:

a liquid reservoir which contains a liquid to be atomized; and a wick comprising a fiber cloth and extending from within said reservoir to a location above an upper surface of said reservoir, said wick being folded over at said location.

17. A refill container according to claim 16, wherein said wick is formed of cotton.

18. A refill container according to claim 17, wherein said wick is formed as a broadcloth weave.

19. A refill container according to claim 18, wherein said wick has a thread count of about 68×68 and a density of about 7.2 grams per 100 square inches.

20. A refill container according to one of claims 16–19, wherein said wick has a pair of tails extending into the reservoir.

\* \* \* \* \*

UNITED STATES PATENT AND TRADEMARK OFFICE
CERTIFICATE OF CORRECTION

PATENT NO.    : 6,293,474 B1
DATED         : September 25, 2001
INVENTOR(S)   : Thomas A. Helf, Edward J. Martens III and David A. Tomkins It is certified that error appears in the above-identified patent and that said Letters Patent is hereby corrected as shown below:

<u>Column 8,</u>
Line 26, replace "2-4" with -- 2-4 and 8 --.
Line 27, replace "wick" with -- wick element --.
Line 29, replace "2-4" with -- 2-4 and 8 --.

Signed and Sealed this

Thirtieth Day of April, 2002

Attest:

Attesting Officer

JAMES E. ROGAN
*Director of the United States Patent and Trademark Office*